US00PP24709P2

(12) United States Plant Patent
Volmary

(10) Patent No.: US PP24,709 P2
(45) Date of Patent: Jul. 29, 2014

(54) ***VERBENA* PLANT NAMED 'VVIDR15-0'**

(50) Latin Name: ***Verbena* hybrid**
Varietal Denomination: 'VVIDR15-0'

(76) Inventor: Hubertus Volmary, Munster (DE)

( * ) Notice: Subject to any disclaimer, the term of this patent is extended or adjusted under 35 U.S.C. 154(b) by 9 days.

(21) Appl. No.: 13/506,672

(22) Filed: May 7, 2012

(51) Int. Cl.
*A01H 5/00* (2006.01)

(52) U.S. Cl.
USPC ..... Plt./308

(58) Field of Classification Search
USPC ..... Plt./308
See application file for complete search history.

*Primary Examiner* — Kent L Bell
(74) *Attorney, Agent, or Firm* — Cassandra Bright

(57) ABSTRACT

A new and distinct *Verbena* cultivar named 'VVIDR15-0' is disclosed, characterized by a compact, trailing plant habit, flexible stems and distinctive bright red flowers. The new variety is a *Verbena*, typically produced as a garden or container plant.

1 Drawing Sheet

Latin name of the genus and species: *Verbena* hybrid.
Variety denomination: 'VVIDR15-0'.

BACKGROUND OF THE INVENTION

The new cultivar is a product of a planned breeding program. The new variety originated from a cross pollination of the seed parent, an unnamed, unpatented proprietary selection of *Verbena* hybrid with the pollen parent a different unnamed, unpatented *Verbena* hybrid. The crossing was made during the Summer of 2009, at a research greenhouse in Munster, Germany. 'VVIDR15-0' was discovered by the inventor, Hubertus Volmary, a citizen of Germany, at the same research greenhouse during the Spring of 2010.

Asexual reproduction of the new cultivar 'VVIDR15-0' was first performed in Munster Germany, at a commercial greenhouse by vegetative cuttings in Summer of 2010. 'VVIDR15-0' has since produced several generations and has shown that the unique features of this cultivar are stable and reproduced true to type.

SUMMARY OF THE INVENTION

The cultivar 'VVIDR15-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VVIDR15-0'. These characteristics in combination distinguish 'VVIDR15-0' as a new and distinct *Verbena* cultivar:

1. Compact, trailing plant habit.
2. Highly floriferous plants.
3. Flexible, non-brittle stems.
4. Distinctive bright red flowers.

PARENTAL COMPARISON

Plants of the new cultivar 'VVIDR15-0' are similar to the female parent in most horticultural characteristics. However, 'VVIDR15-0' differs in producing a compact, trailing plant, whereas the seed parent has a mounding plant habit. Additionally, the seed parent flowers are a different color than the new variety.

Plants of the new cultivar 'VVIDR15-0' are similar to the male parent in most horticultural characteristics. However, 'VVIDR15-0' differs in having a trailing, compact plant habit, whereas the pollen has a distinctively upright plant habit.

COMMERCIAL COMPARISON

'VVIDB12-0' can be compared to the unpatented commercial variety *Verbena* hybrid 'Lan Reda07' U.S. Plant Pat. No. 18,986. Plants of 'Lan Reda07' are similar to plants of 'VVIDR15-0' in most horticultural characteristics, however, plants of 'VVIDR15-0' are more dense and compact in habit and produce a darker colored flower, with more resistance to fading.

BRIEF DESCRIPTION OF THE PHOTOGRAPH

The accompanying photograph in FIG. 1 illustrates in full color a typical plant of 'VVIDR15-0' grown outdoors in Oxnard, Calif. This plant is approximately 2 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2001, except where general terms of ordinary dictionary significance are used. The following observations and measurements describe 'VVIDR15-0' plants in a commercial greenhouse in Oxnard, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Verbena* hybrid 'VVIDR15-0'.

PROPAGATION

Propagation method: Vegetative Cuttings.
Time to initiate roots: About 5 to 7 days at 20.degree. C. to 25.degree. C.
Root description: Fine, densely fibrous.

PLANT

Pot size of plant described: 6 inch pot.
Age of plant described: Approximately 2 months from a rooted cutting.
Height: Approximately 9 cm from soil line of pot to top of foliar plane. Approximately 16 cm from soil line of pot to top of uppermost flowers.
Plant spread: Approximately 40 cm.
Growth rate: Rapid.
Growth habit: Spreading.
Branching characteristics: Free branching.
Length of primary lateral branches: Average 13 cm.
Diameter of lateral branches: Approximately 0.4 cm.
Quantity of primary lateral branches: Approximately 30.
Characteristics of primary lateral branches:
*Color*.—Near RHS Yellow-Green 144B.
*Texture*.—Hirsute. Hairs less than 1 mm, colored near RHS White 155D. Stems also heavily ridged.
*Strength*.—Very strong.
Internode length: Average 2.8 cm.

FOLIAGE

Leaf:
*Arrangement*.—Opposite.
*Quantity*.—Approximately 8 to 10 fully expanded leaves per primary lateral branch with approximately 8 less developed leaves.
*Average length*.—3.8 cm.
*Average width*.—2.6 cm.
*Shape of blade*.—Deltoid, with deep lobes.
*Apex*.—Acute.
*Base*.—Truncate.
*Margin*.—Somewhat crenate, with moderate lobes.
*Texture of top surface*.—Hirsute.
*Texture of bottom surface*.—Puberulent, hirsute along main vein.
*Aspect*.—Very slightly undulate.
*Color*.—Young foliage upper side: Near RHS Green 137A. Young foliage under side: Near RHS Green 137C. Mature foliage upper side: Near RHS Green 137A. Mature foliage under side: Near RHS Green 138B.
*Venation*.—Type: Palmate. Venation color upper side: Near RHS Green 143C. Venation color under side: Near RHS Yellow-Green 144D.
*Attachment*.—Stalked.
*Petiole*.—Length: Average 0.7 cm. Diameter: Average 0.15 cm. Texture: Pubescent. Color: Upper surface: Near RHS Yellow-Green 144C. Lower surface: Near RHS Yellow-Green 144C.

FLOWER

Natural flowering season: Spring and Summer.
Inflorescence and flower type and habit: Flat top umbel.
Individual flower form: Salverform.
Individual flowers per umbel: Average 12 fully opened flowers with 12 buds.
Umbels per plant: More than 20 umbels with open flowers, on a mature plant.
*Umbel size*.—Depth: 3.5 cm to 4.5 cm. Diameter: 5.5 cm to 8.9 cm.
Flower longevity on plant: Approximately 1 week for individual flowers, approximately 3 weeks for entire umbel.
*Individual flower size*.—Depth: 3.0 cm. Diameter: 2.0 cm.
Persistent or self-cleaning: Self-cleaning.
Bud:
*Shape*.—Oblong.
*Length*.—1.8 cm.
*Diameter*.—0.4 cm.
*Color*.—Near RHS Red 46A.
Corolla:
*Petals* (*measured from separation at top of tube*).—Number: 5. Length: Approximately 1.1 cm. Width: Approximately 0.9 cm. Tube Opening Diameter: Approximately 0.15 cm. Tube/throat Length: Approximately 2.2 cm. Shape: Overall deltoid. Deep lobe at apex. Average lobe depth 0.2 cm. Aspect: Flat. Margin: Entire. Texture: Velvety. Apex: 2 obtuse lobes.
*Color*.—When opening: Upper surface: Near RHS Red 46A. Lower surface: Near RHS Red 46A. Fully opened: Upper surface: Near RHS Red 46B, base near Red 53A. Lower surface: Near RHS Red 46C, base White N155A. Fading: Upper surface: Near RHS Red 46A, base near Red 53A. Lower surface: Near RHS Red 53A, base White N155A.
Throat:
*Outer surface color*.—Near RHS Green-White 157C. Flushed Red 46C near top.
*Texture*.—Smooth.
*Interior tube color*.—Near RHS Green-White 157D.
Calyx:
*Form*.—Funnelform. Sepals fused into a single structure, individual sepals indistinguishable.
*Length*.—Approximately 1.4 cm.
*Diameter*.—Approximately 0.3 cm.
*Sepal quantity*.—5 fully fused.
*Sepal texture*.—Puberulent.
*Apex*.—Acute.
*Color*.—Near RHS Green 138A.
*Fragrance*.—None.
Peduncle:
*Length*.—Average 3.8 cm.
*Diameter*.—0.2 cm.
*Color*.—Near RHS Yellow-Green 144B.
*Texture*.—Hirsute. Hairs less than 1 mm.
Pedicel:
*Length*.—Average 0.5 cm.
*Diameter*.—0.1 cm.
*Color*.—Near RHS Yellow-Green 144B.
*Texture*.—Pubescent.

REPRODUCTIVE ORGANS

*Stamens*.—Number (per flower): 4. Filament length: Not measurable, fused to corolla tube. Anthers: Shape: Globular. Length: Approximately 0.1 cm. Color: Near RHS Yellow-Green 154A. Pollen: Amount: Scant. Color: Near RHS Green-Yellow 1B.
*Pistils*.—Quantity per flower: 1. Length: Approximately 1.9 cm. Style: Length: Approximately 1.6 cm. Color: Near RHS Green-White 157D. Stigma: Shape: Linear. Color: Near Yellow-Green 154A. Ovary: Length: Approximately 0.2 cm. Color: Near Yellow-Green 143C.

OTHER CHARACTERISTICS

Seeds and fruits: Not observed to date.

Disease/pest resistance: Neither resistance nor susceptibility to normal diseases and pests of *Verbena* has been observed.

Temperature tolerance: Tolerates temperatures from approximately −1° C. to 32° C.

Drought tolerance: No tolerance for drought.

What is claimed is:

1. A new and distinct cultivar of *Verbena* plant named 'VVIDR15-0' as herein illustrated and described.

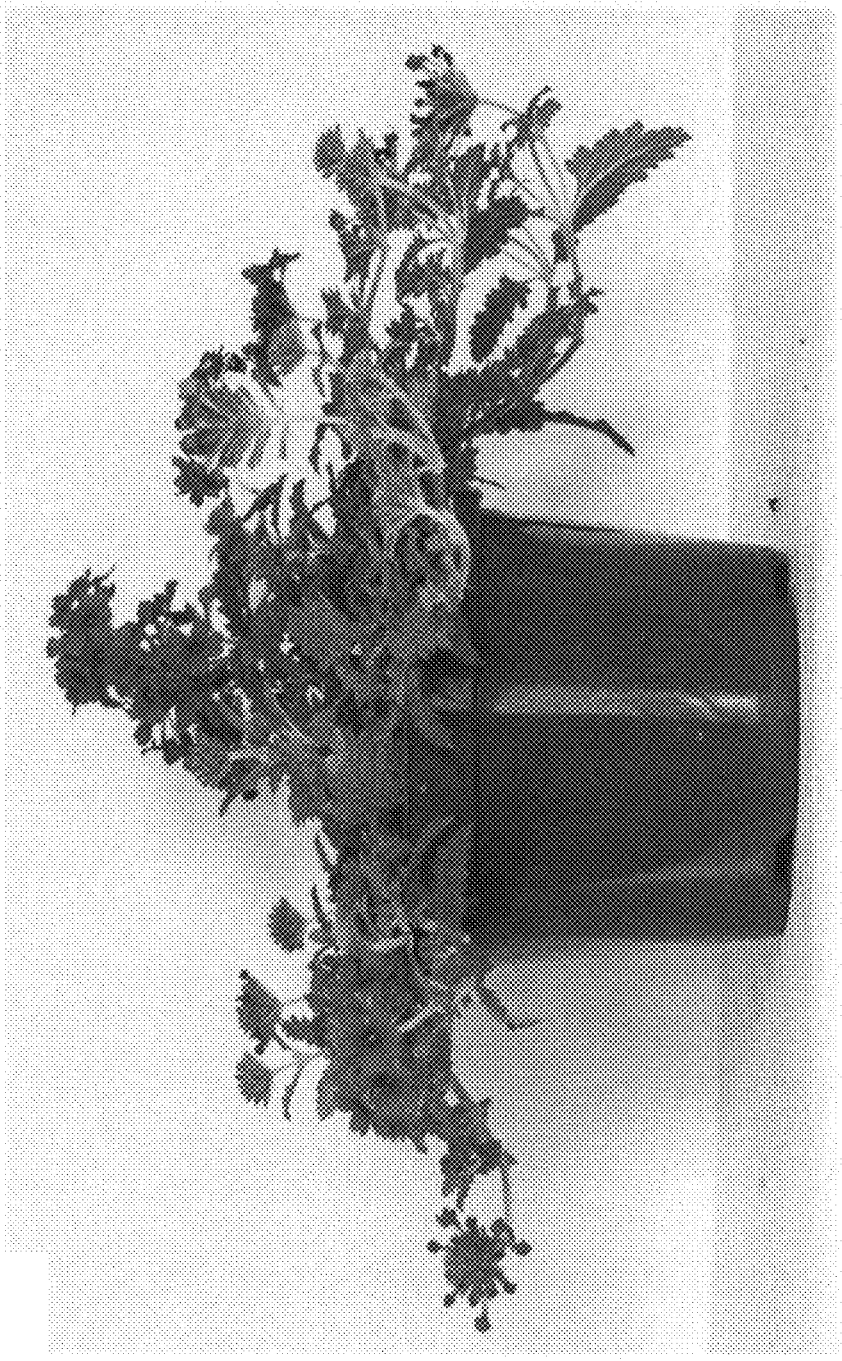

* * * * *